United States Patent
Doi et al.

(10) Patent No.: US 8,168,809 B2
(45) Date of Patent: May 1, 2012

(54) 2-METHYL-3-(3,4-METHYLENEDIOXY-PHENYL)PROPANAL, AND METHOD FOR PRODUCTION THEREOF

(75) Inventors: Takashi Doi, Yamaguchi (JP); Yoshihiro Yoshida, Yamaguchi (JP); Eiji Sajiki, Chiba (JP); Satoru Fujitsu, Yamaguchi (JP)

(73) Assignee: Ube Industries, Ltd., Ube-shi (JP)

( * ) Notice: Subject to any disclaimer, the term of this patent is extended or adjusted under 35 U.S.C. 154(b) by 331 days.

(21) Appl. No.: 12/526,697

(22) PCT Filed: Feb. 14, 2008

(86) PCT No.: PCT/JP2008/052442
§ 371 (c)(1),
(2), (4) Date: Aug. 11, 2009

(87) PCT Pub. No.: WO2008/099882
PCT Pub. Date: Aug. 21, 2008

(65) Prior Publication Data
US 2010/0121085 A1  May 13, 2010

(30) Foreign Application Priority Data
Feb. 15, 2007 (JP) .................... 2007-034177

(51) Int. Cl.
*C07D 317/54* (2006.01)
(52) U.S. Cl. ........................................ 549/446
(58) Field of Classification Search ............ 549/446
See application file for complete search history.

(56) References Cited

U.S. PATENT DOCUMENTS

| | | | |
|---|---|---|---|
| 3,008,968 A | 11/1961 | Beets et al. | |
| 3,185,629 A | 5/1965 | Beets et al. | |
| 2006/0004213 A1 | 1/2006 | Shirai et al. | |
| 2006/0069273 A1 | 3/2006 | Shirai et al. | |

FOREIGN PATENT DOCUMENTS

| | | |
|---|---|---|
| GB | 841921 | 7/1960 |
| JP | 55 141437 | 11/1980 |
| JP | 57 45124 | 3/1982 |
| JP | 10 120674 | 5/1998 |
| JP | 2004 269376 | 9/2004 |
| JP | 2005 239619 | 9/2005 |
| JP | 2005 239620 | 9/2005 |
| JP | 2006 104151 | 4/2006 |
| WO | 2004 054997 | 7/2004 |
| WO | 2006 120639 | 11/2006 |

OTHER PUBLICATIONS

U.S. Appl. No. 12/529,719, filed Sep. 3, 2009, Doi, et al.
U.S. Appl. No. 13/214,408, filed Aug. 22, 2011, Doi, et al.

*Primary Examiner* — Taofiq A Solola
(74) *Attorney, Agent, or Firm* — Oblon, Spivak, McClelland, Maier & Neustadt, L.L.P.

(57) ABSTRACT

Disclosed are: (1) a method for producing 2-methyl-3-(3,4-methylenedioxyphenyl)propanal, which comprises the step of providing a reaction mixture containing 1-acetoxy-2-methyl-3-(3,4-methylenedioxyphenyl)-1-propene by a process for reacting 1,2-methylenedioxybenzene with 2-methyl-3,3-diacetoxypropene or a process for reacting 1,2-methylenedioxybenzene, methacrolein and acetic anhydride with one another; subjecting the reaction mixture to hydrolysis or transesterification with an alcohol to provide a reaction mixture containing 2-methyl-3-(3,4-methylenedioxyphenyl)propanal; and purifying by distilling the reaction mixture, wherein a high boiling point compound contained in the reaction mixture is removed by a specific procedure; and (2) 2-methyl-3-(3,4-methylenedioxyphenyl)-propanal produced by the method, which has an acetic acid content of a less than 40 ppm, is useful as a perfume, and has a high purity.

19 Claims, No Drawings

2-METHYL-3-(3,4-METHYLENEDIOXY-PHENYL)PROPANAL, AND METHOD FOR PRODUCTION THEREOF

TECHNICAL FIELD

The present invention relates to 2-methyl-3-(3,4-methylenedioxyphenyl)propanal that is useful as a perfume (fragrance) and has a high purity, and a method for production thereof.

BACKGROUND ART

It is ordinarily known that odor characteristics of a perfume largely depend on a compound having an aroma and kinds of a slight amount of impurities contained therein or additives added separately. Changes of the formulation or composition of the substances may produce a novel aroma as a perfume or may produce an unpleasant smell. Therefore, the quality of the compound having an odor and the kind and compositional ratio of the minor component contained therein are substantially important for determining the value of the perfume product. Accordingly, a purification step is very important to obtain a perfume compound generating an aroma, on producing a perfume product.

As a purification method of a perfume compound, separation of impurities by distillation or cryogenic separation, removal of impurities by adsorption, etc. have been known. However, special equipments may be often required in the method other than distillation, and for example, the adsorption method involves some problems, such as quality deterioration caused by elution of the adsorbent itself to the product. Otherwise, the purification by distillation can be easily carried out, but in the case where a target perfume compound is a high boiling point fraction, it is necessary to discard a large amount of the initial distillation fraction for preventing low boiling point impurities from being mixed therein, thereby providing a problem of decreasing the yield. Furthermore, under the heating condition, a prolonged period of distillation causes a decomposition of the perfume compound, and side reactions increasing impurities, and the impurities are mixed in the target product to finally provide a problem of deteriorating the quality and the aroma.

2-Methyl-3-(3,4-methylenedioxyphenyl)propanal is an ingredient of marine perfume that is widely used in an ordinary perfumery and cosmetics, such as perfume (eau de cologne), soap, shampoo, conditioner, detergent, cosmetics, perfume spray, fragrance material, etc. (disclosed, for example, in Non-patent Document 1).

As a method for producing 2-methyl-3-(3,4-methylenedioxyphenyl)propanal, such methods have been known as a method of carrying out finally hydrogenation reaction of 2-methyl-3-(3,4-methylenedioxyphenyl)-2-propenal via heliotropin from obtained safrole purified from sassafras oil (disclosed, for example, in Patent Document 1), a method of producing from 1-acetoxy-2-methyl-3-(3,4-methylenedioxyphenyl)-1-propene (disclosed, for example, in Patent Documents 2 and 3), and so on. Patent Documents 4 to 7 disclose a method of producing 2-methyl-3-(3,4-methylenedioxyphenyl)propanal from 1,2-methylenedioxybenzene as a starting material.

Patent Document 2 discloses that 1,2-methylenedioxybenzene and 2-methyl-3,3-diacetoxypropene are reacted to synthesize 1-acetoxy-2-methyl-3-(3,4-methylenedioxyphenyl)-1-propene, and then the compound is hydrolyzed to provide 2-methyl-3-(3,4-methylenedioxyphenyl)propanal as the target product. However, there is no description regarding to impurities and aroma, which are important for a perfume product, of the obtained 2-methyl-3-(3,4-methylenedioxyphenyl)propanal.

[Non-patent Document 1] Angew. Chem. Int. Ed., vol.39(17), p.2980 (2000)
[Patent Document 1] U.S. Pat. No. 3,008,968
[Patent Document 2] JP-A-57-45124
[Patent Document 3] JP-A-2006-104151
[Patent Document 4] JP-A-55-141437
[Patent Document 5] JP-A-2005-239619
[Patent Document 6] WO 2004/054997
[Patent Document 7] WO 2006/120639

DISCLOSURE OF THE INVENTION

Technical Problem

The inventors have synthesized 2-methyl-3-(3,4-methylenedioxyphenyl)propanal according to the method disclosed in Patent Document 2, and also have synthesized 1-acetoxy-2-methyl-3-(3,4-methylenedioxyphenyl)-1-propene and then synthesized 2-methyl-3-(3,4-methylenedioxyphenyl)propanal according to the method disclosed in Patent Documents 4 and 7, but have confirmed that the compounds obtained by these methods did not have a sufficient aroma that is satisfactory as a perfume product. As a result of investigations on the factor deteriorating the aroma, it has been found that by-produced acetic acid provides a problem. Although the formation process of the acetic acid is not clear, it has been confirmed that Reaction by-products, which are by-produced from 1-acetoxy-2-methyl-3-(3,4-methylenedioxyphenyl)-1-propene and the high boiling point compound in the subsequent step, are the major source of the acetic acid upon synthesis of 1-acetoxy-2-methyl-3-(3,4-methylenedioxyphenyl)-1-propene. Furthermore, it has also been confirmed that a slight amount of 2-methyl-3-(3,4-methylenedioxyphenyl)propanal is decomposed to produce acetic acid.

An object of the present invention is to provide 2-methyl-3-(3,4-methylenedioxyphenyl)propanal that has high purity enough to use as a perfume, and a method for efficiently producing the same.

Solution to Problem

As a result of intensive investigations made by the inventors for solving the problems, it has been found that the problems on aroma are solved by controlling a concentration of less than 40 ppm of acetic acid in 2-methyl-3-(3,4-methylenedioxyphenyl)propanal.

The present invention relates to a first invention [1] (production method) and a second invention [2] (substance), as shown below.

[1] A method for producing 2-methyl-3-(3,4-methylenedioxyphenyl)propanal comprising:

Step (1): carrying out a process (A) for reacting 1,2-methylenedioxybenzene represented by the following formula (1) with 2-methyl-3,3-diacetoxypropene represented by the following formula (2) or a process (B) for reacting 1,2-methylenedioxybenzene, methacrolein and acetic anhydride, thereby providing a reaction mixture containing 1-acetoxy-2-methyl-3-(3,4-methylenedioxyphenyl)-1-propene represented by the following formula (3);

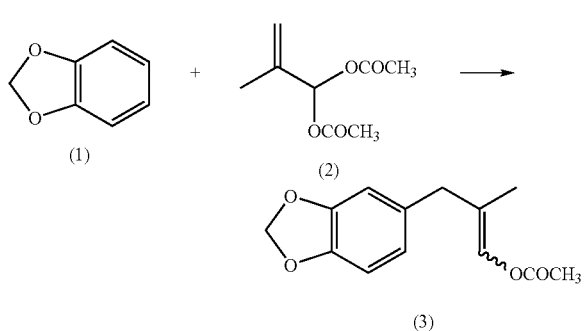

Step (2): providing a reaction mixture containing 2-methyl-3-(3,4-methylenedioxyphenyl)propanal represented by the following formula (4) by hydrolysis reaction or ester exchange reaction with an alcohol of subjecting 1-acetoxy-2-methyl-3-(3,4-methylenedioxyphenyl)-1-propene represented by the formula (3) obtained in the step (1); and

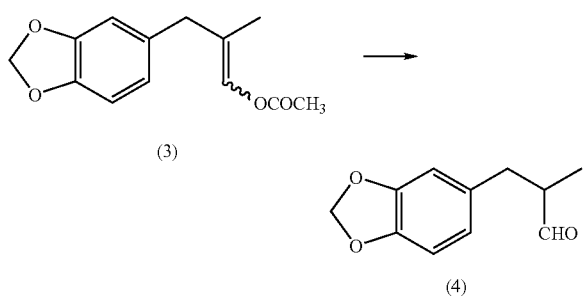

Step (3): purifying by distillation of the reaction mixture obtained in the step (2), wherein the method further comprising at least one of the following procedures (a) to (d):

Procedure (a): after the step (1), removing a compound having a boiling point higher than 1-acetoxy-2-methyl-3-(3,4-methylenedioxyphenyl)-1-propene from the reaction mixture containing the compound (formula (3)), thereby providing a crude product containing the compound (formula (3));

Procedure (b): after the step (2), removing a compound having a boiling point higher than 2-methyl-3-(3,4-methylenedioxyphenyl)propanal from the reaction mixture containing the compound (formula (4)), thereby providing a crude product containing the compound (formula (4));

Procedure (c): carrying out purification by distillation in the step (3) at 210° C. or less of a liquid temperature in a distillation vessel; and Procedure (d): after the step (3), carrying out washing, and neutralization or neutralization and adsorption.

[2] 2-Methyl-3-(3,4-methylenedioxyphenyl)propanal having less than 40 ppm of acetic acid, which produced by the method according to the above [1].

Advantageous Effects of Invention

According to the present invention, 2-methyl-3-(3,4-methylenedioxyphenyl)propanal that has high purity enough to use as a perfume, and a method for producing the same are provided efficiently. 2-Methyl-3-(3,4-methylenedioxyphenyl)propanal obtained by the method of the present invention, for example, provides a more fresh and clear aroma as compared to the products obtained by the methods from safrole or heliotropin as starting materials disclosed in Patent Document 1, and thus has a new aroma that is distinguished from the conventional products.

BEST MODE FOR CARRYING OUT THE INVENTION

The method for producing 2-methyl-3-(3,4-methylenedioxyphenyl)propanal of the present invention comprises the steps (1) to (3) and further comprises at least one of the operations (a) to (d).

The steps (1) to (3) and the procedures (a) to (d) of the present invention will be described.

Step (1)

The step (1) is a step of carrying out a process (A) for reacting 1,2-methylenedioxybenzene represented by the following formula (1) with 2-methyl-3,3-diacetoxypropene represented by the following formula (2) or a process (B) for reacting 1,2-methylenedioxybenzene, methacrolein and acetic anhydride, thereby providing a reaction mixture containing 1-acetoxy-2-methyl-3-(3,4-methylenedioxyphenyl)-1-propene represented by the following formula (3).

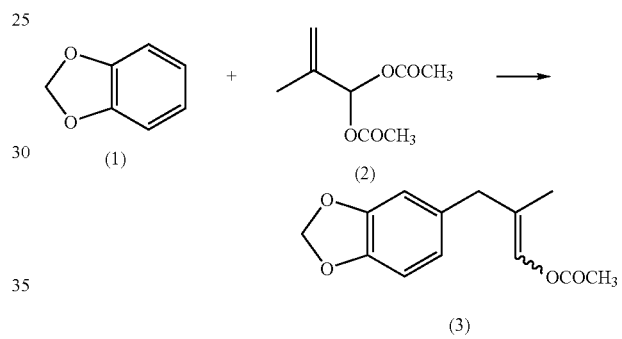

[Process (A)]
(Production of 2-Methyl-3,3-Diacetoxypropene)

The production method of 2-methyl-3,3-diacetoxypropene (formula (2)) used as a raw material of the process (A) is not particularly limited. For example, it can be produced by a process of reacting methacrolein with acetic anhydride in the presence of a catalyst (see JP-A-61-151152; "JP-A" means unexamined published Japanese patent publication).

The reaction process used in this invention, for example, includes a continuous process, a semi-continuous process, a batch process and so on, and any of them may be employed.

In the case of reacting methacrolein and acetic anhydride, a compound having Lewis acidity or a Bronsted acid may be used as a catalyst.

Examples of the Lewis acidic compound include a halogenated boron compound, such as boron trifluoride, boron trichloride, boron tribromide, boron triiodide, boron trifluoride monoacetic acid complex, boron trifluoride diacetic acid complex, boron trifluoride diethyl ether complex, boron trifluoride tetrahydrofuran complex, boron trifluoride acetonitrile complex, boron trifluoride dihydrate, boron trifluoride n-butyl ether complex, boron trifluoride dimethyl ether complex, boron trifluoride methanol complex, boron trifluoride phenol complex, boron trifluoride phosphoric acid complex, etc.; a metal halide, such as aluminum fluoride, aluminum chloride, aluminum bromide, aluminum iodide, gallium fluoride, gallium chloride, gallium bromide, gallium iodide, indium fluoride, indium chloride, indium bromide, indium iodide, scandium chloride, scandium bromide, scandium iodide, yttrium chloride, yttrium bromide, yttrium iodide, titanium tetrachloride, titanium tetrabromide, titanium tetraiodide, zirconium tetrachloride, zirconium tetrabromide, zirconium tetraiodide, hafnium tetrachloride, hafnium tetrabromide, hafnium tetraiodide, iron trifluoride, iron trichloride, iron tribromide, iron triiodide, ruthenium trifluoride, ruthenium trichloride, ruthenium tribromide, ruthenium triiodide, zinc fluoride, zinc chloride, zinc bromide, zinc iodide, cadmium fluoride, cadmium chloride, cadmium bromide, cadmium iodide, mercury fluoride, mercury chloride, mercury bromide, tin fluoride, tin chloride, tin bromide, tin iodide, antimony fluoride, antimony chloride, antimony bromide, antimony iodide, trihalide of a lanthanoid of an atomic number of from 57 to 71, etc.; copper triflate, copper trifluoroacetate, silver triflate, silver trifluoroacetate, zinc triflate, zinc trifluoroacetate, cadmium triflate, cadmium trifluoroacetate, tin triflate, tin trifluoroacetate, scandium triflate, scandium trifluoroacetate, yttrium triflate, yttrium trifluoroacetate, triflate and trifluoroacetate of a lanthanoid of an atomic number of from 57 to 71, etc.

Examples of the Bronsted acid include hydrogen fluoride, hydrochloric acid, hydrogen bromide, hydrogen iodide, trifluoroacetic acid, acetic acid, oxalic acid, phosphoric acid, sulfuric acid, methanesulfonic acid, toluenesulfonic acid, etc.

The Lewis acidic compounds or the Bronsted acids may be used solely or in combination of two or more kinds thereof.

The amount of the catalyst used is not particularly limited, and is generally used in a catalytic amount, for example, an equivalent amount or less for methacrolein. However, in the case where the reaction rate is low, or the reaction does not proceed, the catalyst may be used exceeding over an equivalent molar amount.

A solvent is generally not used, but a solvent may be used if needed.

The molar ratio of methacrolein and acetic anhydride is not particularly limited, and the ratio of acetic anhydride/methacrolein (molar ratio) is generally from 0.5 to 2.5, and preferably from 1.0 to 1.5.

The reaction temperature is also not particularly limited, and is generally from −30 to 65° C., and preferably from 0 to 40° C.

After completing the reaction, the resulting 2-methyl-3,3-diacetoxypropene is generally purified, for example, by washing with water, distillation and so on, and then used as a raw material for the step (1), with or without purification.

(Production of 1-Acetoxy-2-Methyl-3-(3,4-Methylenedioxyphenyl)-1-Propene)

The production method of 1-acetoxy-2-methyl-3-(3,4-methylenedioxyphenyl)-1-propene in the process (A) is not particularly limited, and it can be synthesized, for example, by the method disclosed in Patent Document 2 and 4 to 7.

The reaction process used in the production method includes a continuous process, a semi-continuous process, a batch process and so on, and any of them may be employed.

The molar ratio of 1,2-methylenedioxybenzene (formula (1)) for 2-methyl-3,3-diacetoxypropene (formula (2)); (1,2-methylenedioxybenzene/2-methyl-3,3-diacetoxypropene) is not particularly limited, and is generally from 0.5 to 50, preferably from 2 to 10, and more preferably from 3 to 6.

In the case of reacting 2-methyl-3,3-diacetoxypropene (formula (2)) with 1,2-methylenedioxybenzene (formula (1)), the compound having Lewis acidity or the Bronsted acid may be used as a catalyst. The amount of the catalyst used is not particularly limited, and is generally preferably from 0.001 mol or more and less than 1 mol, more preferably from 0.003 to 0.85 mol, further preferably from 0.004 to 0.50 mol, and particularly preferably from 0.005 to 0.40 mol, per 1 mol of 2-methyl-3,3-diacetoxypropene. However, in the case where the reaction rate is low, or the reaction does not proceed, the catalyst may be used exceeding over an equivalent molar amount.

The reaction temperature of 2-methyl-3,3-diacetoxypropene and 1,2-methylenedioxybenzene is generally from −10 to 80° C., and preferably from 10 to 60° C. In the case where the temperature exceeds over 80° C., 1-acetoxy-2-methyl-3-(3,4-methylenedioxyphenyl)-1-propene as the product starts to be decomposed, and in the case where the temperature is less than −10° C., it is not preferred since the reaction rate may be lowered and the productivity deteriorates.

After completing the reaction, a post-treatment, such as decomposition, washing and so on, may be carried out for removing a by-product and the catalyst from the resulting reaction mixture. The reaction mixture may be subjected to the subsequent step only by decomposing the catalyst by adding an acid, a base or a salt, without water washing, and so on.

[Process (B)]

The process (B) is to react 1,2-methylenedioxybenzene, methacrolein and acetic anhydride. The procedure for the process (B) is not particularly limited, and synthesis of 1-acetoxy-2-methyl-3-(3,4-methylenedioxyphenyl)-1-propene may be carried out by the method disclosed in Patent Document 7, for example.

The reaction process used in the production method includes a continuous process, a semi-continuous process, a batch process and so on, and any of them may be employed.

The molar ratio of methacrolein and acetic anhydride is not particularly limited, and the ratio of acetic anhydride/methacrolein (molar ratio) is generally from 0.5 to 2.5, and preferably from 1.0 to 1.5.

The molar ratio of methacrolein and 1,2-methylenedioxybenzene is not particularly limited, and the ratio of 1,2-methylenedioxybenzene/methacrolein (molar ratio) is generally from 0.5 to 50, preferably from 2 to 10, and more preferably from 3 to 6.

In the case of reacting 1,2-methylenedioxybenzene (formula (1)), methacrolein and acetic anhydride, the compound having Lewis acidity or the Bronsted acid may be used as a catalyst. The amount of the catalyst used, the reaction temperature and the post-treatment after completing the reaction are the same as those in the production conditions for 1-acetoxy-2-methyl-3-(3,4- methylenedioxyphenyl)-1-propene described in the process (A).

In the process (A) and the process (B) in the step (1), after completing the reaction, the resulting reaction mixture contains unreacted 1,2-methylenedioxybenzene (formula (1)) and a group of compounds having higher boiling point than 1-acetoxy-2-methyl-3-(3,4-methylenedioxyphenyl)-1-propene (which are hereinafter referred to as "high boiling point compounds A") in addition to 1-acetoxy-2-methyl-3-(3,4-methylenedioxyphenyl)-1-propene (formula (3)) as the target product.

These reaction mixtures can be purified by a conventional method, such as extraction, filtration, condensation, distillation, recrystallization, crystallization, column chromatography and so on, and in consideration of industrial manufactures, impurities are preferably removed by distillation or crystallization. The removal of the unreacted 1,2-methylenedioxybenzene may be carried out simultaneously with the removal of the high boiling point compounds A (procedure (a)), but is preferably carried out prior to the procedure (a). Distillation for removing the unreacted 1,2-methylenedioxybenzene from the resulting reaction mixture is generally carried out from 40 to 175° C. (from 1 to 760 torr), and preferably from 50 to 150° C. (from 3 to 300 torr), in consideration of the boiling points of 1,2-methylenedioxybenzene (109° C. at 80 torr) and 1-acetoxy-2-methyl-3-(3,4-methylenedioxyphenyl)-1-propene as the target product (170° C. at 5 torr). The unreacted 1,2-methylenedioxybenzene recovered by distillation can be reused in the step (1).

Herein, the high boiling point compounds A are a mixture of various compounds, and contain 1,2-bis(3-acetoxy-2-methyl-2-propenyl)-4,5-methylenedioxybenzene (formula (5)) as a major component, and compounds such as polymers derived from the methacrolein or the 2-methyl-3,3-diacetoxypropene, etc.

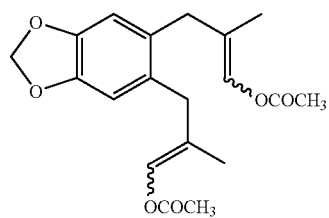

(5)

(Removal of High Boiling Point Compounds A)

The procedure (a) of removing the high boiling point compounds A is preferably carried out after removing (recovering) the unreacted 1,2-methylenedioxybenzene (formula (1)). The amount of 1,2-bis(3-acetoxy-2-methyl-2-propenyl)-4,5-methylenedioxybenzene (formula (5)) contained in the reaction mixture after removing 1,2-methylenedioxybenzene depends on the molar ratio of 1,2-methylenedioxybenzene (formula (1)) to 2-methyl-3,3-diacetoxypropene (formula (2)), and is generally about from 3 to 60% by weight in the case where the ratio of 1,2-methylenedioxybenzene/2-methyl-3,3-diacetoxypropene (molar ratio) is from 1 to 10.

By removing the high boiling point compounds A, the concentration of acetic acid contained in 2-methyl-3-(3,4-methylenedioxyphenyl)propanal (formula (4)) as the final product can be considerably decreased, thereby providing 2-methyl-3-(3,4-methylenedioxyphenyl)propanal that has a fresh and clear aroma as compared to the conventional products. Furthermore, the reaction yield in the step (2) as the subsequent step can be considerably improved.

The reaction mixture containing the high boiling point compounds A may be reacted in the subsequent steps (steps (2) and (3)) without the procedure (a), but in this case, impurities derived from the high boiling point compounds A are further generated in the step (2). When the step (3) is carried out including the impurities, the impurities may be mixed in 2-methyl-3-(3,4-methylenedioxyphenyl)propanal as the target product, and acetic acid may by-produced from the impurities during distillation, whereby it is difficult to control the concentration of the acetic acid within a desired range. As a result, high purified 2-methyl-3-(3,4-methylenedioxyphenyl)propanal may not be obtained with high yield, and therefore it is important and preferred to carry out the procedure (a) to provide a crude product containing 1-acetoxy-2-methyl-3-(3,4-methylenedioxyphenyl)-1-propene (formula (3)) as a main content. It is more preferred to carry out both the procedure (a) and the procedure (c) described later. In the case where the procedure (a) is not carried out, it is preferred to carry out at least one of the procedures (b) and (c) described later, and it is more preferred to carry out both of the procedures (b) and (c).

The procedure (a) for removing the high boiling point compounds A is preferably purification by distillation or crystallization.

(Purification by Distillation)

The purification method for removing the high boiling point compounds A may be carried out either by simple distillation or by rectification. The distillation process may be any of a batch process, a semi-continuous process and a continuous process.

The distillation apparatus is preferably equipped with a rectification column from the standpoint of decreasing the amount of the high boiling point compounds A mixed in the main fraction. The number of the rectification column and the opportunity (frequency) of distillation are not particularly limited.

The rectification column can be the one that is conventionally used in purification by distillation, such as a tray rectification column, a packed rectification column, etc. In this case, a thin film evaporator or a falling liquid film evaporator, which undergoes a short residence time, is preferably used for suppressing the thermally decomposition of 1-acetoxy-2-methyl-3-(3,4-methylenedioxyphenyl)-1-propene.

In the case where a packed rectification column is used, the kind of the packing is not particularly limited. Since 2-methyl-3-(3,4-methylenedioxyphenyl)propanal becomes liable to be decomposed when the distillation temperature is high, it is preferred to use a structured packing in order to make the difference in pressure between the head part and the bottom part of the rectification column smaller, for preventing the liquid temperature of the distillation vessel from being set at a high temperature.

The structured packing that can be used, for example, includes "Sulzer Packing" (formed wire mesh type) and "Mellapak" (formed porous metallic sheet type) manufactured by Sulzer Chemtech, Ltd., "Gempack" manufactured by Koch Glitsch, LP, "MontzPak" manufactured by Julius Montz GmbH, "Goodroll Packing" manufactured by Nippon Filcon Co., Ltd., "Honeycombpack" manufactured by NGK Insulators, Ltd., "Impulse Packing" manufactured by Nagaoka Co., Ltd., MC Pack (formed wire mesh type or formed metallic sheet type) and Technopack, etc. The material for the rectification column and the packing used, for example, includes ones that are used in conventional distillation purification, such as stainless steel, Hastelloy, ceramics, resins, etc.

The method of heating in distillation is not particularly limited, and a heat exchanger that is conventionally used, such as a jacket type, a coil type, a falling liquid film type, a thin film type, etc., may be used. For example, it is preferred to use a heating device, such as a falling liquid film reboiler connected to the rectification column, since the thermally decomposition of 1-acetoxy-2-methyl-3-(3,4-methylenedioxyphenyl)-1-propene (formula (3)) in the reaction mixture can be suppressed during distillation.

The pressure upon distillation in the procedure (a) is not particularly limited, and is generally from 0.1 to 100 torr (from 0.013 to 13.332 kPa), and preferably from 1 to 20 torr (from 0.133 to 2.666 kPa). The distillation temperature of the main fraction depends on the pressure, and is generally from 120 to 240° C., and preferably from 150 to 200° C., in consideration of the fact that 1-acetoxy-2-methyl-3-(3,4-methylenedioxyphenyl)-1-propene (formula (3)) has a boiling point of 170° C. at 5 torr (0.666 kPa) and 1,2-bis(3-acetoxy-2-methyl-2-propenyl)-4,5-methylenedioxybenzene (formula (5)) as the high boiling point compound has a boiling point of 236° C. at 5 torr (0.666 kPa).

It is preferred in the distillation carried out in the procedure (a) that 1-acetoxy-2-methyl-3-(3,4-methylenedioxyphenyl)-1-propene (formula (3)) as the target product is isolated into the distilled fraction, and the high boiling point compounds A are isolated into the residue in the distillation vessel after distillation.

The actual numbers of plates in the distillation rectification column is generally from 1 to 200 plates, preferably from 2 to 120 plates, and more preferably from 3 to 70 plates.

The reflux ratio may be determined after confirming the isolation state on the rectification columns. In the case where the number of plates is small, the isolation efficiency is lowered. On the contrary, an excessive number of plates is not preferred. The reflux ratio (refluxed amount/distilled amount) in distillation is generally from 0 to 50, preferably from 0.1 to 30, and more preferably from 1 to 15. An excessive reflux ratio is not preferred since decomposition of 1-acetoxy-2-methyl-3-(3,4-methylenedioxyphenyl)-1-propene and other side reaction may be accelerated by heating.

By carrying out the distillation in the procedure (a) under these conditions, a crude product of 1-acetoxy-2-methyl-3-(3,4-methylenedioxyphenyl)-1-propene (formula (3)) can be obtained that preferably has a content of the high boiling point compounds A of 15 wt % or less, more preferably 10 wt % or less, further preferably 5 wt % or less, and particularly preferably 1 wt % or less.

By carrying out the distillation in the procedure (a) under these conditions, a crude product of 1-acetoxy-2-methyl-3-(3,4-methylenedioxyphenyl)-1-propene (formula (3)) can be obtained that preferably has 1,2-bis(3-acetoxy-2-methyl-2-propenyl)-4,5-methylenedioxybenzene as the major component of the high boiling point compounds A of 9.5 mol % or less, more preferably 6.0 mol % or less, further preferably 3.0 mol % or less, and particularly preferably 0.5 mol % or less.

(Crystallization)

The method and apparatus for crystallization for removing the high boiling point compounds A are not particularly limited.

The crystallization method includes, for example, conventional crystallization methods, such as crystallization by cooling, crystallization by concentrating, crystallization from a mixed solvent system, and so on, and a seed crystal may be added during crystallization.

The solvent used in this invention is also not particularly limited, and examples thereof include an alcohol solvent, such as methanol, ethanol, etc.; a ketone solvent, such as acetone, methyl ethyl ketone, etc.; an ether solvent, such as diisopropyl ether, etc.; a hydrocarbon solvent, such as n-hexane, heptane, etc.; an aromatic hydrocarbon compound as a solvent, such as toluene, xylene, etc. The solvents may be used solely or in combination of two or more kinds thereof.

For improving the crystal characteristics and the yield of 1-acetoxy-2-methyl-3-(3,4-methylenedioxyphenyl)-1-propene (formula (3)), a poor solvent, such as n-hexane, etc., may be added in a suitable amount in advance or may be added during crystallization.

Crystals of 1-acetoxy-2-methyl-3-(3,4-methylenedioxyphenyl)-1-propene thus obtained are subjected to ordinary solid-liquid separation, then washed and dried. The crystals may be carried out the subsequent step (2) without drying, in the case where the solvent used in crystallization does not disturb the step (2). The method of solid-liquid separation include, for examples, conventional methods, such as filtration under increased pressure, filtration under reduced pressure, centrifugal separation, and so on.

The drying may be carried out under ambient pressure or reduced pressure. The drying temperature is generally from 20 to 55° C., and preferably from 30 to 50° C., in consideration of the melting point of 1-acetoxy-2-methyl-3-(3,4-methylenedioxyphenyl)-1-propene of from 58 to 59° C.

The reaction yield in the subsequent step (2) is significantly improved by the above-mentioned crystallization procedure.

As shown in above, the reaction yield in the subsequent step (2) is improved, in the case where the content of the high boiling point compounds A such as 1,2-bis(3-acetoxy-2-methyl-2-propenyl)-4,5-methylenedioxybenzene (formula (5)), etc., which contained in 1-acetoxy-2-methyl-3-(3,4-methylenedioxyphenyl)-1-propene (formula (3)), is smaller.

By removing the high boiling point compounds A in the step (1), the content of acetic acid contained in 2-methyl-3-(3,4-methylenedioxyphenyl)propanal as the final product is decreased to less than 40 ppm, thereby providing 2-methyl-3-(3,4-methylenedioxyphenyl)propanal that has a fresh and clear aroma as being different from the conventional products.

Step (2)

The step (2) is a step of providing a reaction mixture containing 2-methyl-3-(3,4-methylenedioxyphenyl)propanal represented by the following formula (4) by hydrolysis reaction or ester exchange reaction with an alcohol of subjecting 1-acetoxy-2-methyl-3-(3,4-methylenedioxyphenyl)-1-propene represented by the formula (3) obtained in the step (1).

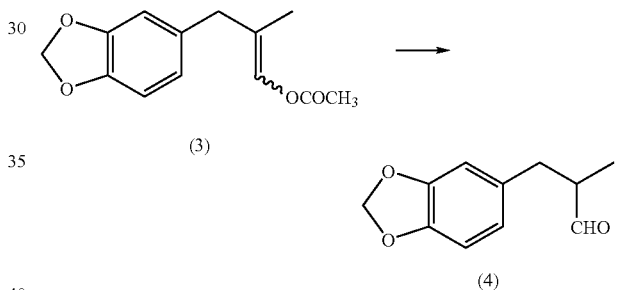

(Hydrolysis Reaction)

The process of the hydrolysis may be any of a batch process, a semi-continuous process and a continuous process. The hydrolysis may be carried out by adding water, and an organic solvent may be used in order to improve mixing of water and 1-acetoxy-2-methyl-3-(3,4-methylenedioxyphenyl)-1-propene. The kind and the amount of the organic solvent used are not particularly limited, except for disturbing the reaction. The organic solvent includes, for example, an alcohol compound, such as methyl alcohol, ethyl alcohol, isopropyl alcohol, n-propyl alcohol, n-butyl alcohol, isobutyl alcohol, sec-butyl alcohol, tert-butyl alcohol, ethylene glycol, propylene glycol, etc.; a ketone compound, such as acetone, methyl ethyl ketone, diethyl ketone, methyl isobutyl ketone, etc.; an aliphatic carboxylic acid, such as acetic acid, propionic acid, butyric acid, etc.; an aliphatic carboxylate ester, such as methyl acetate, ethyl acetate, methyl propionate, ethyl propionate, etc.; and a polar solvent, such as acetonitrile, tetrahydrofuran, N,N-dimethylformamide, N,N-dimethylimidazolidinone, N-methylpyrrolidone, dimethylsulfoxide, hexamethylphosphoric triamide, etc. The solvents may be used solely or in combination of two or more kinds thereof. The organic solvent may be recovered after completing the reaction, and then reused in next time.

A catalyst used in the hydrolysis includes, for example, an acidic catalyst and a basic catalyst.

The acidic catalyst includes, for example, hydrogen fluoride, hydrochloric acid, hydrogen iodide, oxalic acid, sulfuric acid, phosphoric acid, sodium dihydrogen phosphate, sodium hydrogen phosphate, nitric acid, formic acid, acetic acid, oxalic acid, propionic acid, an acidic ion exchange resin, zeolite having acidic points, etc.

The basic catalyst includes, for example, a hydroxide of an alkali metal or an alkaline earth metal (such as lithium hydroxide, sodium hydroxide, potassium hydroxide, rubidium hydroxide, cesium hydroxide, magnesium hydroxide, calcium hydroxide, strontium hydroxide, etc.); a carbonate salt of a hydroxide of an alkali metal or an alkaline earth metal (such as lithium carbonate, sodium carbonate, potassium carbonate, rubidium carbonate, cesium carbonate, magnesium carbonate, calcium carbonate, strontium carbonate, etc.); an alkoxide of an alkali metal or an alkaline earth metal (such as lithium methoxide, sodium methoxide, potassium methoxide, rubidium methoxide, cesium methoxide, calcium methoxide and magnesium methoxide); a carboxylate salt of an alkali metal or an alkaline earth metal (such as sodium acetate, potassium acetate, sodium oxalate, potassium oxalate); a phosphate salt of an alkali metal or an alkaline earth metal (such as sodium phosphate, etc.); a basic ion exchange resin; zeolite having basic points, etc.

The acidic catalyst and the basic catalyst may be used solely or in combination of two or more kinds thereof.

The amount of the catalyst used in the present invention depends on the kind thereof, and is generally 1 mol or less, preferably from 0.001 to 0.5 mol, and more preferably from 0.005 to 0.3 mol, per mol of 1-acetoxy-2-methyl-3-(3,4-methylenedioxyphenyl)-1-propene. In the case where the reaction rate is low, or the reaction does not proceed very well, however, the catalyst may be used in an amount over the equivalent amount of 1-acetoxy-2-methyl-3-(3,4-methylenedioxyphenyl)-1-propene.

In the hydrolysis, the amount of water used in the present invention is generally from 1 to 50 mol, preferably from 1.5 to 30 mol, and more preferably from 3 to 20 mol, per mol of 1-acetoxy-2-methyl-3-(3,4-methylenedioxyphenyl)-1-propene.

The temperature of the hydrolysis reaction depends on the kind and amount of the catalyst and the kind of the solvent, and is preferably from 20 to 120° C., and more preferably from 30 to 100° C.

(Transesterification with Alcohol)

In the step (2), 1-acetoxy-2-methyl-3-(3,4-methylenedioxyphenyl)-1-propene (formula (3)) obtained in the step (1) may be subjected to transesterification (ester exchange reaction) with an alcohol. In the reaction, an acetate ester of the alcohol is by-produced.

The process of the ester exchange reaction may be any of a continuous process, a semi-continuous process and a batch process.

The alcohol used in the ester exchange reaction includes, for example, a monoalcohol, such as methanol, ethanol, isopropyl alcohol, n-propyl alcohol, n-butanol, isobutanol, sec-butyl alcohol, tert-butyl alcohol, n-octanol, etc.; a polyol, such as ethylene glycol, propylene glycol, 1,4-butanediol, glycerin, etc. The alcohol may be used solely or in combination of two or more kinds thereof.

The amount of the alcohol is not particularly limited, and is generally from 1 to 50 mol, preferably from 1.2 to 30 mol, and more preferably from 1.5 to 20 mol, per mol of 1-acetoxy-2-methyl-3-(3,4-methylenedioxyphenyl)-1-propene. The unreacted alcohol may be recovered and reused in the ester exchange reaction in next time.

A catalyst used in the ester exchange reaction is not particularly limited, and an acidic catalyst, a basic catalyst, an organic metal catalyst, etc. may be used. The acidic catalyst and the basic catalyst include, for example, those described for the hydrolysis reaction.

Examples of the organic metal catalysts include a zinc compound, such as zinc carboxylate (e.g., zinc acetate), zinc acetylacetonate, etc.; a manganese compound, such as manganese carboxylate (e.g., manganese acetate), manganese acetylacetonate, etc.; a nickel compound, such as nickel carboxylate (e.g., nickel acetate), nickel acetylacetonate, etc.; an antimony compound, such as antimony carboxylate (e.g., antimony acetate), antimony alkoxide, etc.; a zirconium compound, such as zirconium alkoxide (e.g., zirconium propoxide, zirconium butoxide), zirconium acetylacetonate, etc.; a titanium compound, such as titanium alkoxide (e.g., titanium tetraethoxide, titanium tetraisopropoxide, titanium tetrabutoxide), etc.; a tin compound (e.g., dibutyltin oxide, dibutyltin diacetate, dibutyltin dilaurate, tin oxide). The organic metal catalyst may be used solely or in combination of two or more kinds thereof.

The amount of the catalyst for the ester exchange reaction depends on the kind of the catalyst, and is generally 1 mol or less, preferably from 0.001 to 0.5 mol, and more preferably from 0.005 to 0.3 mol, per mol of 1-acetoxy-2-methyl-3-(3,4-methylenedioxyphenyl)-1-propene.

The reaction may be carried out with an organic solvent optionally added for increasing the solubility of the catalyst. The organic solvent used in this invention may be appropriately determined depending on the kind of the catalyst used, and is not particularly limited within performing increasing of the solubility of the catalyst and not disturbing the reaction. For example, the organic solvents include a ketone compound, such as acetone, methyl ethyl ketone, diethyl ketone, methyl isobutyl ketone, etc.; an aliphatic carboxylic acid, such as acetic acid, propionic acid, butyric acid, etc.; an aliphatic carboxylate ester, such as methyl acetate, ethyl acetate, methyl propionate, ethyl propionate, etc.; a halogen solvent, such as methylene chloride, chloroform, chlorobenzene, etc.; and a polar solvent, such as acetonitrile, tetrahydrofuran, N,N-dimethylformamide, N,N-dimethylimidazolidinone, N-methylpyrrolidone, dimethylsulfoxide, hexamethylphosphoric triamide, etc. The solvent may be used solely or in combination of two or more kinds thereof. The organic solvent may be recovered after completing the reaction, and then reused in next time.

The temperature of the ester exchange reaction depends on the kind of the alcohol and the amount of the catalyst, and is generally from 0 to 150° C., preferably from 20 to 120° C., and more preferably from 30 to 100° C.

In the case where 1-acetoxy-2-methyl-3-(3,4-methylenedioxyphenyl)-1-propene (formula (3)) remains in a large amount after completing the reaction of the step (2), the compound (formula (3)) is gradually decomposed in the step (3), which may generate acetic acid, and therefore, the conversion ratio of 1-acetoxy-2-methyl-3-(3,4-methylenedioxyphenyl)-1-propene is preferably 90 wt % or more, more preferably 95 wt % or more, and further preferably 98 wt % or more.

The reaction mixture in the step (2) contains the catalyst used, and it is preferred as a post-treatment that the catalyst is neutralized with an acid or a base, or the reaction mixture is washed with water, an acidic aqueous solution or a basic aqueous solution for removing the catalyst. Without performing neutralization or washing, water, an alcohol or the organic solvent, which used in the reactions, may be removed by distillation, or 2-methyl-3-(3,4-methylenedioxyphenyl)propanal may be purified by distillation. But in that case, the targeted 2-methyl-3-(3, 4-methylenedioxyphenyl)propanal may be cause some problems by decomposing by the remaining catalyst.

In the hydrolysis reaction, acetic acid is formed as a by-product, and the acetic acid can be effectively removed from the reaction mixture by washing with the solution as a post-treatment.

(Removal of High Boiling Point Compounds B)

In the case where the step (2) is carried out without carrying out the procedure (a) in the present invention, the alcohol, water, the acetate ester by-produced, and the organic solvent, which used in the reactions, are removed from the resulting reaction solution after completing the reaction, and then the procedure (b) is preferably carried out for removing a group of compounds as by-products having higher boiling point than 2-methyl-3-(3,4-methylenedioxy-phenyl)propanal (boiling point: 158° C. at 10 torr) (which are hereinafter referred to as "high boiling point compounds B"). The procedure (b) can prevent a generation of acetic acid from the high boiling point compounds B in the subsequent step (3).

The high boiling point compounds B herein are a mixture of various compounds, for example, including unreacted 1-acetoxy-2-methyl-3-(3,4-methylenedioxyphenyl)-1-propene, 1,2-bis(3-acetoxy-2-methyl-2-propenyl)-4,5-methyl-enedioxybenzene (formula (5)), impurities derived from these compounds, such as 1,2-bis(2-methyl-3-oxopropyl)-4,5-methylenedioxybenzene (formula (6)) and 1-(3-acetoxy-2-methyl-2-propenyl)-2-(2-methyl-3-oxopropyl)-4,5-methyl-enedioxybenzene (formula (7)), compounds formed by decomposing these compounds, etc. In addition, compounds, such as polymers derived from methacrolein, 2-methyl-3,3-diacetoxypropene, 1-acetoxy-2-methyl-3-(3,4-methylene-dioxyphenyl)propene and 2-methyl-3-(3,4-methylenediox-yphenyl)-propanal, etc. are also contained.

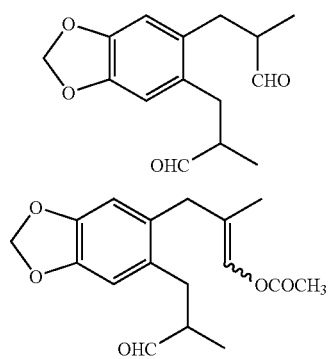

(6)

(7)

As the procedure (b) for removing the high boiling point compounds B, conventional methods may be employed, such as extraction, filtration, condensation, distillation, recrystallization, crystallization, column chromatography and so on, and a purification by distillation is most preferred.

(Purification by Distillation)

The process and the opportunity of the purification purification, the kind of the rectification column, etc. are the same as those in the distillation purification described for the procedure (a).

Since 2-methyl-3-(3,4-methylenedioxyphenyl)propanal (formula (4)) is liable to be decomposed thermally, the distillation purification is preferably carried out with a thin film evaporator, a falling liquid film evaporator, etc., which undergoes a short residence time. Charging for distillation and taking out fractions are preferably carried out under an inert gas.

In the case of using a packed rectification column, the kind of the packing is not particularly limited. Since 2-methyl-3-(3,4-methylenedioxyphenyl)propanal is decomposed significantly, the distillation temperature is higher, and the yield is lower. It is preferred to use a structured packing in order to make the difference in pressure between the head part and the bottom part of the rectification column smaller, for preventing the liquid temperature of the distillation vessel from being set at a high temperature. The kind and the specification of the structured packing that can be used are the same as those described for the procedure (a).

While the distillation conditions on removing the high boiling point compounds B are not particularly limited, the pressure at the head part of the rectification column is preferably from 0.1 to 100 torr (from 0.013 to 13.33 kPa), and more preferably from 1 to 20 torr (from 0.133 to 2.66 kPa), and the distillation temperature is preferably from 120 to 230° C., and more preferably from 130 to 190° C., although it varies depending on the pressure upon distillation.

The removal of the high boiling point compounds B by distillation is preferably carried out in such a manner that 2-methyl-3-(3,4-methylenedioxyphenyl)propanal (formula (4)) as the target product is isolated into the distilled fraction, and the high boiling point compounds B are isolated into the residue in the distillation vessel.

The substantial number of plates and the reflux ratio in the distillation purification are the same as in the procedure (a), and is generally from 1 to 200 plates, preferably from 2 to 100 plates, and more preferably from 3 to 60 plates, for each of the rectification columns, and the reflux ratio (refluxed amount/distilled amount) is generally from 0 to 50, preferably from 0.5 to 20, and more preferably from 1 to 10. A reflux ratio of less than 0.1 lowers the isolation efficiency, and an excessive reflux ratio is not preferred since decomposition of 1-methyl-3-(3,4-methylenedioxyphenyl)propanal and other side reaction may be accelerated.

By carrying out the distillation in the procedure (b) under above-mentioned conditions, a crude product of 2-methyl-3-(3,4-methylenedioxyphenyl)propanal can be obtained that preferably has a content of the high boiling point compounds B of 5 wt % or less, more preferably 2 wt % or less, and further preferably 0.5 wt % or less.

Step (3)

The step (3) is a step of providing high purified 2-methyl-3-(3,4-methylenedioxyphenyl)propanal by purification by distillation of the reaction mixture containing 2-methyl-3-(3, 4-methylenedioxyphenyl)propanal obtained in the step (2).

(Purification by Distillation)

The process and the opportunity of the purification by distillation, the kind of the rectification column, the kind of the packing in the step (3) are the same as those in the distillation purification described for the procedures (a) and (b). Since 2-methyl-3-(3,4-methylene-dioxyphenyl)propanal (formula (4)) is gradually decomposed thermally during distillation, a continuous process and a semi-continuous process, which undergoes a short residence time, are preferred.

The actual numbers of plates and the reflux ratio (refluxed amount/distilled amount) in the distillation purification in the step (3) are the same as those in the procedure (b). A reflux ratio of less than 0.1 lowers the isolation efficiency, and an excessive reflux ratio is not preferred, since decomposition of 1-methyl-3-(3,4-methylenedioxyphenyl)propanal and other reaction may be accelerated.

(Procedure (c))

In the step (3), the purification by distillation is preferably carried out at 210° C. or less of a liquid temperature in the distillation vessel of the distillation apparatus (procedure (c)).

More specifically, the temperature is preferably the range from 100 to 210° C., more preferably from 140 to 210° C., and further preferably from 150 to 200° C., at the head part of the rectification column, under reduced pressure (from 0.1 to 100 torr (from 0.013 to 13.332 kPa)). Upon collecting the final product (upon distilling the main fraction), the liquid temperature in the distillation vessel of the distillation apparatus is 210° C. or less, preferably the range from 125 to 210° C., more preferably from 130 to 200° C., further preferably from 135 to 190° C., particularly preferably from 140 to 185° C., and most preferably from 145 to 180° C. The temperature exceeding over 210° C. is not preferred, since 2-methyl-3-(3,4-methylene-dioxyphenyl)propanal itself is decomposed to form acetic acid and then this acid may be mixed in the main fraction, even though the high boiling point by-product and impurities do not present in the solution in the distillation vessel.

High vacuum is required, in the case of distilling with a lower liquid temperature in the distillation vessel. In this case, it is necessary to use a special vacuum pump with high performance and to use a rectification column with a larger size therefor, which is not economically advantageous. Accordingly, for providing 2-methyl-3-(3,4-methylenedioxyphenyl)propanal with high purity as the final product, it is preferred to carry out the purification by distillation under the conditions of the procedure (c).

Particularly, in the case where the distillation purification is carried out by a batch process, 2-methyl-3-(3,4-methylenedioxyphenyl)propanal is liable to be decomposed since the residence time thereof in the rectification column is prolonged, and the amount of acetic acid formed may be increased, as compared to the continuous rectification process. Accordingly, the distillation temperature is preferably the range from 130 to 210° C., and more preferably from 140 to 185° C., in the batch process. Charging for distillation and taking out fractions are preferably carried out under an inert gas.

2-Methyl-3-(3,4-methylenedioxyphenyl)propanal with high purity containing less than 40 ppm of acetic acid can be obtained by the distillation purification of the step (3).

(Procedure (d))
(Washing, Neutralization, or Neutralization and Adsorption)

A crude product containing 2-methyl-3-(3,4-methylenedioxyphenyl)propanal having an acetic acid content of 40 ppm or more may also be obtained by the distillation purification of the step (3). Accordingly, the obtained crude product may be subjected to the procedure (d) of washing with water, washing and neutralization with an aqueous solution of a basic compound, or neutralization and adsorption. 2-Methyl-3-(3,4-methylenedioxyphenyl)propanal, having an acetic acid decreased to less than 40 ppm, can be obtained as the final product by the procedure (d).

(Washing with Water, or Washing and Neutralization with Aqueous Solution of Basic Compound)

The amount of water used for washing in the procedure (d) is not particularly limited, and is generally the range from 0.1 to 50 times, preferably from 0.2 to 10 times, more preferably from 0.3 to 5 times, and further preferably from 0.5 to 1.5 times, with respect to 1 g of 2-methyl-3-(3,4-methylenedioxyphenyl)propanal obtained in the step (3). While the crude product may be washed only with water, the crude product may be washed with an aqueous solution of a salt, such as sodium chloride, sodium sulfate, etc., in the case where it is difficult to separate into the organic phase and the aqueous phase.

By washing with an aqueous solution of a basic compound, such as sodium hydroxide, potassium hydroxide, sodium carbonate, potassium carbonate, etc., acetic acid is neutralized, and an acetic acid salt thus formed can be distributed to the aqueous phase, thereby decreasing the acetic acid content.

The opportunity of washing is not particularly limited, and washing operations with water, an aqueous solution of a salt, and an aqueous solution of a basic compound may be combined. The temperature is not particularly limited upon liquid separation after washing, and the organic phase and the aqueous phase can be favorably separated when the temperature is from 40 to 70° C.

2-Methyl-3-(3,4-methylenedioxyphenyl)propanal may contain water after washing with water or washing with an aqueous solution of a basic compound. Accordingly, the water may be removed if desired, for example, by distillation, drying under reduced pressure, or dehydration by drying agent. The method for removing water is preferably distillation.

The distillation condition is preferably a pressure of from 10 torr to ordinary pressure, but there is no particular limitation, in the case where the temperature is at 210° C. or less. The residue in the distillation vessel after removing water may be the final product, or may be again subjected to distillation purification under the same conditions as in the procedure (c) in the step (3).

(Neutralization, or Neutralization and Adsorption)

By contacting with a basic compound or passing through a column filled by them, particularly a basic ion exchange resin, acetic acid in 2-methyl-3-(3,4-methylenedioxy-phenyl)propanal obtained in the step (3) may be neutralized the containing acetic acid, or the resulting acetate salt removed by filtration or adsorption with the basic ion exchange resin. Thus the content of acetic acid can be decreased to less than 40 ppm. The operation is generally carried out from 0 to 80° C.

According to the present invention, 2-methyl-3-(3,4-methylenedioxyphenyl)propanal having less than 40 ppm of acetic acid can be efficiently produced, and a perfumer recognized that acetic acid contained in 2-methyl-3-(3,4-methylenedioxyphenyl)propanal in an amount of less than 40 ppm does not affect the aroma thereof.

2-Methyl-3-(3,4-methylenedioxyphenyl)propanal obtained by the production method of the present invention has an aroma that is different from 2-methyl-3-(3,4-methylene-dioxyphenyl)propanal produced from safrole or heliotropin.

EXAMPLES

The present invention will be described specifically with reference to examples and comparative examples. In the examples and comparative examples below, "%" means "% by weight" unless otherwise indicated.

In the present invention, [1] the purity of 2-methyl-3-(3,4-methylenedioxyphenyl)propanal, [2] the acetic acid content, and [3] the reaction yield after completing the step (2) and the distillation yield in the step (3) were determined in the following manners.

[1] Purity of 2-Methyl-3-(3,4-methylenedioxyphenyl)Propanal

A high performance liquid chromatography (HPLC) apparatus "CLASS-VP" manufactured by Shimadzu Corporation (analytic column: "TSKgel ODS-80Ts, QA 4.6 mm×250 mm" manufactured by Tosoh Corporation) was used, an eluant of acetonitrile/0.1% phosphoric acid aqueous solution=40/60 (volume ratio) was used, and the apparatus was set at pH 2.5, a flow rate of 1.0 mL/min and a column oven temperature of 40° C. An UV detector was used, the measurement wavelength was 252 nm, and the sample injection amount was 20 μL.

The sample for analysis was prepared by weighing 0.8 g of a sample to be measured to a 50-mL volumetric flask, and then filling the flask by diluting with acetonitrile. 5 mL of the resulting solution was collected by a whole pipette and placed in a 50-mL volumetric flask, and then it was filled by diluting with acetonitrile. The resulting solution was examined for analysis.

[2] Acetic Acid Content

A gas chromatography apparatus "GC-14B" manufactured by Shimadzu Corporation (detector: FID system; analytic column: TC-WAX (0.53 mm×30 m, membrane thickness: 1.0 μm) manufactured by GL Sciences, Inc.) was used, and the content of acetic acid was measured and calculated by the absolute calibration curve method.

0.6 μL of 2-methyl-3-(3,4-methylenedioxyphenyl)-propanal as a target reference was injected by a 1-μL microsyringe. The injection temperature was 220° C., the detector temperature was 260° C., and the column temperature was maintained at 80° C. for 3 minutes, increased to 115° C. at a rate of 5° C. per minute, increased to 230° C. at a rate of 40° C. per minute, and then maintained at 230° C. for 20 minutes.

[3] The reaction yield (%) after completing the step (2) and the distillation yield (%) in the step (3) were calculated by the following equations.

Reaction yield (%) after completing step (2)=[mole of 2-methyl-3-(3,4-methylenedioxyphenyl)propanal/mole of methacrolein, which used in the reaction]×100

Distillation yield (%) in step (3)=[(weight of main fraction/molecular weight of 2-methyl-3-(3,4-methylene-dioxyphenyl)propanal/mole of 2-methyl-3-(3,4-methylene-dioxyphenyl)propanal in charged solution]×100

Example 1

(Production of 2-Methyl-3-(3,4-Methylenedioxyphenyl)Propanal)

[Step (1)]

1,703 g of acetic anhydride and 2.9 g of boron trifluoride diethyl ether complex were placed under a nitrogen gas atmosphere in a 20-L separable flask equipped with a stirrer, a thermometer and a condenser. 1,021 g of methacrolein (purity: 96.1%) was added dropwise thereto while maintaining the liquid temperature in the range from 0 to 20° C. The mixture was stirred at the range from 9 to 11° C. for 2 hours to provide a mixed solution containing 2-methyl-3,3-diacetoxypropene. 8,200 g of 1,2-methylenedioxybenzene was added to the mixed solution, to which 56.9 g of boron trifluoride diethyl ether complex was then gradually added dropwise, and the mixture was stirred at a liquid temperature of from 38 to 41° C. for 4 hours. After completing the reaction, the resulting reaction mixture was washed with water, the organic phase was collected by separation and extraction, and unreacted 1,2-methylenedioxybenzene was recovered by distillation from the organic phase, thereby providing 3,380 g of a residue containing 1-acetoxy-2-methyl-3-(3,4-methylenedioxyphenyl)-1-propene.

The composition of the residue was 82.8% of 1-acetoxy-2-methyl-3-(3,4-methylenedioxyphenyl)-1-propene (formula (3)) and 8.6% of 1,2-bis(3-acetoxy-2-methyl-2-propenyl)-4,5-methylenedioxybenzene (formula (5)).

[Step (2)]

3,044 g of methanol and 25.0 g of potassium carbonate were mixed with the residue, and the mixture was stirred from 30 to 50° C. for 4 hours to carry out ester exchange reaction until the conversion ratio of 1-acetoxy-2-methyl-3-(3,4-methylenedioxyphenyl)-1-propene reached 99%. After completing the reaction, the resulting reaction solution was mixed with 23.6 g of a 75% phosphoric acid aqueous solution, followed by stirring.

Methyl acetate and methanol produced through the reaction were distilled off, and the resulting concentrate was washed with water to provide 2,616 g of a reaction mixture of 2-methyl-3-(3,4-methylenedioxyphenyl)propanal.

The resulting reaction mixture was analyzed by the aforementioned methods. As the result, it had a purity of 78.0% and contained about 20% of the high boiling point compounds B. The reaction yield of 2-methyl-3-(3,4-methylenedioxyphenyl)propanal based on 1-acetoxy-3-(3,4-methylenedioxyphenyl)propene was 88.8%, and the reaction yield of 2-methyl-3-(3,4-methylenedioxyphenyl)propanal based on methacrolein was 75.9%, by HPLC analysis.

Subsequently, 834 g (net amount: 651 g) of 2,616 g of the reaction mixture was distilled with a rectification column (packing: Laboratory Packing EX, trade name, manufactured by Sulzer Chemtech, Ltd., diameter: 25 mm×height: 1,100 mm) with a 1-L flask equipped with a stirrer, a thermometer and a condenser, 32.6 g of an initial fraction was distilled off at a reflux ratio of 7, and then 596 g (net amount: 589 g, purity: 98.9%) of a crude product, which had been removed the high boiling point compounds B, was obtained by the distillation under a pressure of 7 torr (0.933 kPa), a temperature of the bottom part of from 177 to 210° C., a temperature of the head part of from 152 to 153° C. and a reflux ratio of 1 [procedure (b)].

[Step (3)]

The resulting crude product was again distilled with the rectification column with the 1-L flask equipped with the stirrer, the thermometer and the condenser. 110 g of an initial fraction was distilled off at a reflux ratio of 10, and then 450 g of 2-methyl-3-(3,4-methylenedioxyphenyl)-propanal as the final product obtained as the main fraction by the distillation under a pressure from 7 to 8 torr, a temperature of the bottom part from 170 to 180° C., a temperature of the head part from 153 to 154° C. and a reflux ratio of 1 [procedure (c)].

The resulting 2-methyl-3-(3,4-methylenedioxyphenyl)-propanal had a purity of 99.4%, the content of an acetic acid was 19 ppm and a distillation yield was 69.1%.

Upon collecting the main fraction, the distilled fraction was sampled by dividing into 10 fractions, and the fractions were evaluated by perfumers according to the following standard. The results are shown in Table 1.

(Standard for Evaluation)

o: The specimen had no acid smell in the aroma and was able to be used practically as a perfume.

x: The specimen exhibited abnormal odor and was not be able to be used practically as a perfume.

Moreover, the difference in aroma from a commercial product (available from Acros Organics) was also evaluated. The results are shown in Table 1.

o: The specimen had an aroma that was different from the commercially available product.

x: The specimen had the same aroma as the commercially available product.

-: The specimen was not evaluated.

TABLE 1

| | Initial fraction | 1 | 2 | 3 | 7 | 10 | 15 | Total |
|---|---|---|---|---|---|---|---|---|
| Fraction (g) | 110 | 30 | 30 | 30 | 30 | 30 | 30 | 450 |
| HLF purity (%) | 94.59 | 98.89 | 99.04 | 99.13 | 99.38 | 99.56 | 99.75 | 99.39 |
| Acetic acid content (ppm) | 1,735 | 52 | 39 | 28 | 15 | 7 | 5 | 19 |
| Evaluation   Evaluation in odor | X | X | ○ | ○ | ○ | ○ | ○ | ○ |
| Difference in aroma from commercially available product | — | — | ○ | ○ | ○ | ○ | ○ | ○ |

Note:
HLF is an abbreviation of 2-methyl-3-(3,4-methylenedioxyphenyl)propanal.

According to Table 1, it is understood that a specimen having less than 40 ppm of acetic acid was able to be used as a perfume, since abnormal odor was found in the case where the acetic acid content was 40 ppm or more. Furthermore, it is understood that a specimen containing less than 40 ppm of acetic acid was a new perfume that exhibited a fresh and clear aroma that was different from the commercial product. However, the distilled fractions (2, 3, 7, 10 and 15) were not able to be distinguished from each other by slight difference in aroma owing to the difference in acetic acid content (from 5 to 39 ppm).

Example 2

(Production of
2-Methyl-3-(3,4-Methylenedioxy-Phenyl)Propanal)

[Step (1)]

1,736.5 g of acetic anhydride and 4.1 g of boron trifluoride diethyl ether complex were mixed under a nitrogen gas atmosphere in a 20-L separable flask equipped with a stirrer, a thermometer and a condenser. 1,071 g of methacrolein (purity: 94.2%) was added dropwise thereto while maintaining the liquid temperature in the range from 0 to 20° C. The mixture was stirred for 2 hours to provide a mixed solution containing 2-methyl-3,3-diacetoxypropene. 8,200 g of 1,2-methylenedioxybenzene was added to the mixed solution, and then 61.7 g of boron trifluoride diethyl ether complex was gradually dropwised. After completing the dropwise addition, the mixture was stirred at a liquid temperature from 38 to 42° C. for 4 hours. After completing the reaction, the resulting solution was washed with water, the organic phase was collected by separation and extraction, and unreacted 1,2-methylenedioxybenzene was distilled off.

3,589 g of the resulting solution was transferred to a simple distillation apparatus and distilled (pressure: 3 torr, temperature: 182° C.) to provide 3,058 g of a main fraction as a crude product. In the main fraction, the purity of 1-acetoxy-2-methyl-3-(3,4-methylenedioxyphenyl)-1-propene was 94.4%, and the purity of 1,2-bis(3-acetoxy-2-methyl-2-propenyl)-4,5-methylenedioxybenzene (formula (5)) was 1.3% [procedure (a)].

[Step (2)]

3,235 g of methanol and 24.4 g of potassium carbonate were mixed in a 10-L separable flask equipped with a stirrer, a thermometer and a condenser, to which the solution of 1-acetoxy-2-methyl-3-(3,4-methylenedioxyphenyl)-1-propene, which had been heated to the temperature from 78 to 82° C., was gradually dropwised with stirring at 30° C. After completing the dropwise addition, the mixture was stirred at 30 to 50° C. for about 5 hours to carry out ester exchange reaction. The conversion ratio of 1-acetoxy-2-methyl-3-(3,4-methylenedioxyphenyl)-1-propene after completing the reaction was 98.0%. 22.8 g of a 75% phosphoric acid aqueous solution was added to the reaction solution, followed by stirring, and then methanol and methyl acetate by-produced were distilled off under reduced pressure. The resulting concentrate was washed with water to provide 2,424 g of a crude product of 2-methyl-3-(3,4-methylenedioxyphenyl)propanal (purity: 94.1%).

The analysis of the resulting crude product indicated that the reaction yield of 2-methyl-3-(3,4-methylenedioxy-phenyl)propanal based on 1-acetoxy-2-methyl-3-(3,4-methylenedioxyphenyl)-1-propene was 96.2%, and the reaction yield of 2-methyl-3-(3,4-methylenedioxyphenyl)propanal based on methacrolein was 82.4%.

[Step (3)]

Subsequently, 783 g (net amount: 737 g) of the crude product of 2-methyl-3-(3,4-methylenedioxyphenyl)propanal was distilled with a rectification column (packing: Laboratory Packing EX, trade name, manufactured by Sulzer Chemtech, Ltd., diameter: 25 mm×height: 1,100 mm) with a 1-L flask. 189 g of an initial fraction was distilled off at a reflux ratio of 10, and then 480 g of 2-methyl-3-(3,4-methylenedioxyphenyl)propanal (purity: 99.7%, acetic acid content: 6 ppm) as the final product was collected as the main fraction at a pressure of from 6 to 7 torr, a liquid temperature of the distillation vessel of from 172 to 200° C., a temperature of the head part of from 148 to 151° C. and a reflux ratio of 1 (distillation yield: 64.9%) [procedure (c)].

The aroma of the resulting 2-methyl-3-(3,4-methylenedioxyphenyl)propanal contained no acid smell and was evaluated favorably by the perfumers. The distillation yield was 65.1%.

Example 3

(Production of 1-Acetoxy-2-Methyl-3-(3,4-Methylenedioxyphenyl)Propene by Process (B))

22.1 g (300 mmol) of methacrolein, 36.8 g (360 mmol) of acetic anhydride and 171.2 g (1,410 mmol) of 1,2-methylenedioxybenzene were placed and mixed in a 300-mL three-neck flask equipped with a stirring device and a thermometer. 0.97 g (6.0 mmol) of iron(III) chloride (anhydride) was gradually added thereto while maintaining the internal temperature to from 5 to 45° C., followed by stirring for 5 hours. After completing the reaction, 200 mL of water was added to the resulting reaction product, followed by stirring for 10 minutes. Subsequently, after separating the aqueous phase, 200 mL of water was again added to the organic phase, followed by stirring for 10 minutes. The aqueous phase was again separated, and the resulting organic phase was analyzed by HPLC. As a result, the yield amount of 1-acetoxy-2-methyl-3-(3,4-methylenedioxyphenyl)-1-propene was 54.9 g (yield based on methacrolein: 78.1%). The amount of produced 1,2-bis(3-acetoxy-2-methyl-2-propenyl) -4,5-methylenedioxybenzene (formula (5)) was 7.2 g (yield: 7.1%).

Thereafter, the same operations as the procedure (a), the step (2) and the step (3) (procedure (c)) in Example 2 were carried out to provide 27.7 g of 2-methyl-3-(3,4-methylenedioxyphenyl)propanal. The amount of acetic acid contained in the resulting 2-methyl-3-(3,4-methylenedioxy-phenyl)propanal was 18 ppm.

Reference Example 1

(Step (2): Ester Exchange Reaction using Metallic Catalyst)

After carrying out the same procedures as the step (1) and the procedure (a) in Example 2, 2.24 g (70.0 mmol) of methanol and 0.284 g (1.00 mmol) of titanium(IV) isopropoxide were mixed under a nitrogen gas atmosphere in a 25-mL three-neck flask equipped with a stirrer, a thermometer and a condenser. 2.34 g (10.0 mmol) of 1-acetoxy-2-methyl-3-(3,4-methylenedioxyphenyl)-1-propene was gradually dropwised thereto with stirring at 30 to 50° C. After completing the dropwise addition, the mixture was stirred at 30 to 50° C. for about 1 hour. After completing the reaction, the resulting reaction solution was analyzed by HPLC. As a result, the conversion ratio of 1-acetoxy-2-methyl-3-(3,4-methylenedioxyphenyl)-1-propene was 100%, and the selectivity of 2-methyl-3-(3,4-methylenedioxyphenyl)-propanal was 96%.

In the step (2), 2-methyl-3-(3,4-methylenedioxy-phenyl)propanal can be obtained with a high selectivity by ester exchange reaction using a metallic catalyst such as titanium (IV) isopropoxide.

Thereafter, the step (3) and the procedures (c) and (d) in Example 2 may be carried out.

Reference Example 2

1 mL of 2-methyl-3-(3,4-methylenedioxyphenyl)propanal having an acetic acid content of 5 ppm (purity: 99.6%, having been confirmed that no high boiling point compound B was contained) obtained in the same manner as in Example 2 was placed in a 2.5 mL-stainless steel vessel, and was sealed by plugging. Four of the vessels were placed in oil baths at prescribed temperatures (185° C., 200° C., 220° C. and 230° C., respectively) and allowed to stand. After lapsing a prescribed period of time, the vessels were taken out from the oil bath, and the purity of 2-methyl-3-(3,4-methylene-dioxyphenyl)propanal and the acetic acid content were measured. The results obtained are shown in Table 2.

TABLE 2

| Temperature | Amount of compounds | Elapsed time | | | | |
|---|---|---|---|---|---|---|
| | | 0 h | 24 h | 48 h | 72 h | 96 h |
| 185° C. | HLF (wt %) | 99.6 | 99.7 | 99 | 98.6 | 97.4 |
| | Acetic acid (ppm) | 5 | 8 | 10 | 12 | 12 |
| 200° C. | HLF (wt %) | 99.6 | 99.2 | 98.9 | 97.8 | 96.3 |
| | Acetic acid (ppm) | 5 | 17 | 24 | 32 | 36 |
| 220° C. | HLF (wt %) | 99.6 | 98.2 | 96.5 | 95.4 | 93.1 |
| | Acetic acid (ppm) | 5 | 34 | 38 | 44 | 47 |
| 230° C. | HLF (wt %) | 99.6 | 95.7 | 94 | 90.4 | — |
| | Acetic acid (ppm) | 5 | 46 | 36 | 35 | — |

Note:
HLF is an abbreviation of 2-methyl-3-(3,4-methylenedioxyphenyl)propanal.

According to Table 2, it is understood that 2-methyl-3-(3,4-methylenedioxyphenyl)propanal is decomposed significantly and the amount of acetic acid formed is also increased, when the temperature upon distillation is 220° C. or more.

It is also understood that the temperature upon distillation is desirably 210° C. or less, and preferably 200° C. or less, in consideration of Table 1 that abnormal odor is observed when the acetic acid concentration is 40 ppm or more.

Reference Example 3

2-Methyl-3-(3,4-methylenedioxyphenyl)propanal was synthesized in the same manner as in Example 1, and the purification step is carried out in the same manner to collect the main fraction. Thereafter, the liquid temperature in the distillation vessel was heated to 220° C., and then the rectification was finished after confirming that no distillation occurred. 40.0 g of the residue after the distillation was the high boiling point compounds B containing 20.6% of 2-methyl-3-(3,4-methylenedioxyphenyl)-propanal and the residue contained a mixture of various kinds of polymers.

The high boiling point compounds B were added to the 2-methyl-3-(3,4-methylenedioxyphenyl)propanal (purity: 99.6%) obtained by the distillation purification to adjust the content of the high boiling point compounds B to 7.4% and 16%.

The mixtures were examined for time-lapse change in, for example, amount of acetic acid at 185° C. in the same manner as in Reference Example 2. The results are shown in Table 3.

TABLE 3

| Content of high boiling point compounds B | | Elapsed time | | | | |
|---|---|---|---|---|---|---|
| | | 0 h | 24 h | 48 h | 72 h | 96 h |
| 0 wt % | Amount of HLF (wt %) | 99.6 | 99.7 | 99.0 | 98.6 | 97.4 |
| | HLF residual ratio (%) | 100 | 100 | 96.7 | 99.4 | 98.2 |
| | Amount of acetic acid (ppm) | 5 | 8 | 10 | 12 | 12 |
| 7.4 wt % | Amount of HLF (wt %) | 92.6 | 90.7 | 88.6 | 85.6 | 82.4 |
| | HLF residual ratio (%) | 100 | 98.0 | 95.7 | 92.4 | 89.5 |
| | Amount of acetic acid (ppm) | 13 | 46 | 65 | 110 | 118 |
| 16 wt % | Amount of HLF (wt %) | 83.2 | 80.6 | 79.3 | 76.4 | 73.8 |
| | HLF residual ratio (%) | 100 | 96.8 | 95.3 | 91.8 | 88.7 |
| | Amount of acetic acid (ppm) | 26 | 95 | 178 | 196 | 244 |

Note:
HLF is an abbreviation of 2-methyl-3-(3,4-methylenedioxyphenyl)propanal.

According to Table 3, it is understood that it is more preferred that the high boiling point compounds B are removed before providing the final product, since 2-methyl-3-(3,4-methylenedioxyphenyl)propanal is decomposed significantly and the amount of generated acetic acid is increased in the case where the content of the high boiling point compounds B is increased.

Comparative Example 1

(Example Where the Procedures (a) to (d) Were Not Carried Out)

722 g (net amount: 563 g) of 2,616 g of reaction mixture of 2-methyl-3-(3,4-methylenedioxyphenyl)propanal (purity: 78.0%), which had been obtained in the same manner as in Example 1 except that the procedure (b) in the step (2) was not carried out, was purified by distillation by using a rectification column (packing: Sulzer Laboratory Packing EX, trade name, manufactured by Sulzer Chemtech, Ltd., diameter: 25 mm×height: 1,100 mm) with a 1-L flask. A main fraction was obtained after the area percentage of the fraction in gas chromatography reached 99% or more. Upon collecting the initial fraction, the reflux ratio was 10, and the main fraction was distilled at a reflux ratio of 1. During distilling the main fraction, the pressure was from 7 to 8 torr (from 0.933 to 1.066 kPa), the liquid temperature in the distillation vessel was from 175 to 220° C., and the temperature of the head part of a rectification column was from 152 to 153° C.

The initial fraction was 182 g, the main fraction was 320 g, and the purity of 2-methyl-3-(3,4-methylenedioxy-phenyl)propanal was 99.7%. The content of acetic acid was 104 ppm, and it was not able to be used as a perfume, because of the odor containing acid smell significantly. The distillation yield was 56.8%.

It was understood from the results of Comparative Example 1 that even though the purity of 2-methyl-3-(3,4-methylenedioxyphenyl)propanal was as the target product was 99.7%, it was not able to be used as a perfume due to significant acid smell in the case where the acetic acid content was 40 ppm or more (104 ppm).

Example 4

350 g of 2-methyl-3-(3,4-methylenedioxyphenyl)propanal containing 122 ppm of acetic acid was obtained by carrying out the same procedures as in Comparative Example 1. 37.9 g of above-mentioned propanal was placed in a separating funnel, to which 36.5 g of saturated brine was added thereto, and the separating funnel was shaken, followed by allowing to stand for 5 minutes. The organic phase (heavy liquid) was taken out, and the concentration of acetic acid in the resulting organic phase was 21 ppm after measurement. The organic phase was further washed with saturated brine to provide 2-methyl-3-(3,4-methylenedioxyphenyl)propanal having an acetic acid concentration of 6 ppm. The resulting 2-methyl-3-(3,4-methylenedioxyphenyl)propanal had a favorable aroma.

Reference Example 4

46.8 g (195.5 mmol) of 1-acetoxy-2-methyl-3-(3,4-methylenedioxyphenyl)-1-propene (which had a purity of 97.9% and had been confirmed by gas chromatography and liquid chromatography that it contained no 1,2-bis(3-acetoxy-2-methyl-2-propenyl)-4,5-methylenedioxybenzene (formula (5))) and 7.11 g (20.5 mmol) of 1,2-bis(3-acetoxy-2-methyl-2-propenyl)-4,5-methylenedioxybenzene (which provided a content of 1,2-bis(3-acetoxy-2-methyl-2-propenyl)-4,5-methylenedioxybenzene of 9.5 mol %), which had been prepared as same manner as in Example 2, were mixed to provide a mixture in a 200-mL four-neck flask. 52.3 g (1,634 mmol) of methanol was added thereto, and the temperature of the mixed solution was heated to 60° C. with stirring, and then cooled to 40° C. after the mixed solution became homogeneous. 0.53 g (3.8 mmol) anhydrous potassium carbonate was added to the mixed solution gradually, and after completing the addition, the reaction was further carried out at 40° C. for 1.5 hours. After completing the reaction, 0.56 g of 85% phosphoric acid was added for neutralization, and then unreacted methanol and by-produced methyl acetate were distilled off by simple distillation. 37.8 g of water was added to the residue after the simple distillation, followed by stirring at 40 to 50° C. The mixture was then placed in separating funnel, and 42.5 g of an organic phase was obtained. The content of 2-methyl-3-(3,4-methylenedioxyphenyl)propanal in the organic phase was analyzed by HPLC to calculate the reaction yield, which was 85.1%.

The same procedures as above were carried out by using mixtures that were changed in content (mol %) of 1,2-bis(3-acetoxy-2-methyl-2-propenyl)-4,5-methylenedioxybenzene. The results obtained are shown in Table 4.

TABLE 4

| Content of high boiling point compounds*[1] (mol %) | | 0 | 0.4 | 2.9 | 5.8 | 9.5 | 22 |
|---|---|---|---|---|---|---|---|
| Result of reaction | Conversion ratio *2 (%) | 100 | 100 | 100 | 100 | 100 | 100 |
|  | Reaction yield *3 (%) | 99.8 | 97.4 | 93.6 | 90.8 | 85.1 | 71.4 |

*[1](Mole of 1,2-bis(3-acetoxy-2-methyl-2-propenyl)-4,5-methylenedioxybenzene)/[(Mole of 2-methyl-3-(3,4-methylenedioxyphenyl)propanal) + (Mole of 1,2-bis(3-acetoxy-2-methyl-2-propenyl)-4,5-methylenedioxybenzene)] × 100
*2: Conversion ratio of 1-acetoxy-2-methyl-3-(3,4-methylenedioxyphenyl)-1-propene (by HPLC)
*3: Yield of 2-methyl-3-(3,4-methylenedioxyphenyl)propanal In Reference Example 4, the influence of 1,2-bis(3-acetoxy-2-methyl-2-propenyl)-4,5-methylenedioxybenzene (formula (5)), in the case where the procedure (a) in the step (1) were not carried out, was investigated on the step (2). As a result, it was found that when the content of 1,2-bis(3-acetoxy-2-methyl-2-propenyl)-4,5-methylenedioxybenzene was 9.5 mol % or more, the yield of 2-methyl-3-(3,4-methylenedioxyphenyl)propanal as the target product became 85% or less and the content of the high boiling point compounds B tended to be increased. These lead to the demerit that the aroma of the product may be easy to be adversely affected and that the loss upon distillation may be increased.

Industrial Applicability

The present invention provides 2-methyl-3-(3,4-methylenedioxyphenyl)propanal that is useful as a perfume and has a high purity, and its efficient producing method. 2-Methyl-3-(3,4-methylenedioxyphenyl)propanal obtained by the method of the present invention has a new aroma (i.e., fresh and clear aroma) that is distinguished from a product produced from safrole or heliotropin as starting materials.

The invention claimed is:

1. A method for producing 2-methyl-3-(3,4-methylenedioxyphenyl) propanal comprising:

Step (1): carrying out a process (A) for reacting 1,2-methylenedioxybenzene represented by the following formula (1) with 2-methyl-3,3-diacetoxypropene represented by the following formula (2) or a process (B) for reacting 1,2-methylenedioxybenzene, methacrolein and acetic anhydride, thereby providing a reaction mixture containing 1-acetoxy-2-methyl-3-(3,4-methylenedioxyphenyl)-1-propene represented by the following formula (3);

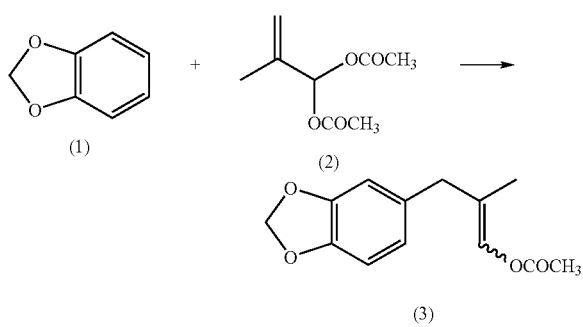

(1)   (2)

(3)

Optionally Step (2), removing a compound having a boiling point higher than 1-acetoxy-2-methyl-3-(3,4-methylenedioxyphenyl)-1-propene from the reaction mixture containing 1-acetoxy-2-methyl-3-(3,4-methylenedioxyphenyl)-1-propene, thereby providing a crude product containing 1-acetoxy-2-methyl-3-(3,4-methylenedioxyphenyl)-1-propene;

Step (3): providing a reaction mixture containing 2-methyl-3-(3,4-methylenedioxyphenyl)propanal represented by the following formula (4) by hydrolysis reaction or ester exchange reaction with an alcohol of subjecting 1-acetoxy-2-methyl-3-(3,4-methylenedioxyphenyl)-1-propene represented by the formula (3) obtained in the step (1);

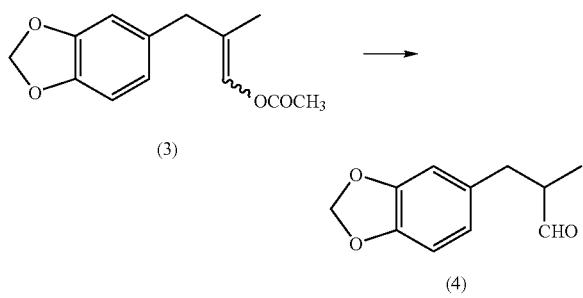

(3)

(4)

Optionally Step (4), removing a compound having a boiling point higher than 2-methyl-3-(3,4-methylenedioxyphenyl)propanal from the reaction mixture, thereby providing a crude product containing 2-methyl-3-(3,4-methylenedioxyphenyl)propanal;

Step (5): purifying by distillation of the reaction mixture obtained in the step (3)

carrying optionally Step (6): carrying out purification by distillation in the step (5) at a liquid temperature in a distillation vessel of 210° C. or less; and optionally Step (7), carrying out washing, and neutralization or neutralization and adsorption;

whereby the process shall comprise at least one of optional steps (2), (4) (6) and (7).

2. The method according to claim 1, wherein Step (2) or Step (4) is carried out.

3. The method according to claim 1, wherein a content of 1,2-bis(3-acetoxy-2-methyl-2-propenyl)-4,5-methylenedioxybenzene is 9.5 mol % or less by carrying out step (2).

4. The method according to claim 1, wherein a conversion ratio of 1-acetoxy-2-methyl-3-(3,4-methylenedioxyphenyl)-1-propene is 98% or more in the step (3).

5. The method according to claim 1, wherein the purification by distillation in the step (5) is carried out under the liquid temperature range from 130 to 210° C. in a distillation vessel.

6. The method according to claim 1, wherein the produced 2-Methyl-3-(3,4-methylenedioxyphenyl)propanal has less than 40 ppm of acetic acid.

7. A method of preparing a perfume composition comprising formulating a perfume composition with 2-methyl-3-(3,4-methylenedioxyphenyl)propanal produced by the method according to claim 1.

8. The method according to claim 1, wherein a 2-methyl-3,3-diacetoxypropene and 1,2-methylenedioxybenzene are reacted at a temperature of from −10 to 80° C.

9. The method according to claim 1, wherein 1,2-methylenedioxybenzene and 2-methyl-3,3-diacetoxypropene are reacted at a ratio of 0.5 to 50.

10. The method according to claim 1, wherein 1,2-methylenedioxybenzene and methacrolein are reacted at a molar ratio of from 0.5 to 50.

11. The method according to claim 1, wherein step (2) is performed by crystallization.

12. The method according to claim 1, wherein step (2) is performed by distillation at a temperature of from 120-240° C. and a pressure of from 0.1 to 100 torr.

13. The method according to claim 1, wherein step (2) is performed by distillation at a reflux ratio of from 1 to 15.

14. The method according to claim 1, wherein step (4) is performed by at least one method selected from the group consisting of extraction, filtration, condensation, distillation, recrystallization, crystallization and column chromatography.

15. The method according to claim 1, wherein step (4) is performed by distillation at a temperature of from 120-230-° C. and a pressure of from 0.1 to 100 torr.

16. The method according to claim 1, wherein step (6) is performed at a temperature of from 100 to 210° C. and a pressure of form 0.1 to 100 torr.

17. The method according to claim 1, wherein step (7) is performed by washing with water.

18. The method according to claim 1, wherein step (7) is performed by washing and neutralizing with an aqueous solution of a basic compound.

19. The method according to claim 1, wherein step (7) is performed by neutralization and adsorption.

* * * * *